(12) United States Patent
Quan et al.

(10) Patent No.: US 11,382,843 B2
(45) Date of Patent: Jul. 12, 2022

(54) ALCOGEL SHEET FOR COSMETIC USE, AND METHOD FOR PRODUCING SAME

(71) Applicant: COSMED PHARMACEUTICAL CO., LTD., Kyoto (JP)

(72) Inventors: Ying-shu Quan, Kyoto (JP); Naoko Kondou, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 73 days.

(21) Appl. No.: 16/096,277

(22) PCT Filed: Apr. 28, 2017

(86) PCT No.: PCT/JP2017/016879
§ 371 (c)(1),
(2) Date: Oct. 24, 2018

(87) PCT Pub. No.: WO2017/188424
PCT Pub. Date: Nov. 2, 2017

(65) Prior Publication Data
US 2019/0142707 A1    May 16, 2019

(30) Foreign Application Priority Data

Apr. 28, 2016  (JP) .............. JP2016-091940
Jun. 4, 2016   (JP) .............. JP2016-112303

(51) Int. Cl.
*A61K 8/04*      (2006.01)
*A61K 8/365*     (2006.01)
(Continued)

(52) U.S. Cl.
CPC ............ *A61K 8/042* (2013.01); *A61K 8/0208* (2013.01); *A61K 8/20* (2013.01); *A61K 8/345* (2013.01);
(Continued)

(58) Field of Classification Search
CPC ........ A61Q 19/00; A61Q 17/04; A61Q 19/08; A61Q 1/14; A61Q 15/00; A61Q 5/00; A61Q 19/02; A61Q 17/005; A61Q 19/007; A61Q 19/10; A61Q 11/00; A61Q 13/00; A61Q 1/12; A61Q 5/12; A61Q 9/02; A61Q 3/00; A61Q 5/06; A61Q 17/02; A61Q 19/001; A61Q 19/002; A61Q 19/008; A61Q 1/04; A61Q 1/06; A61Q 90/00; A61Q 19/06; A61Q 1/00; A61Q 1/02; A61Q 1/08; A61Q 1/10; A61Q 5/02; A61Q 5/04; A61Q 7/00; A61K 8/042; A61K 8/0208; A61K 8/73; A61K 8/731; A61K 8/34; A61K 8/345; A61K 2300/00; A61K 8/34; A61K 2800/88; A61K 8/0212; A61K 8/0216; A61K 9/0014; A61K 9/06; A61K 2800/10; A61K 47/10; A61K 8/65; A61K 8/8147; A61K 9/7007; A61K 47/38; A61K 8/735; A61K 8/86; A61K 2800/242; A61K 31/045; A61K 31/555; A61K 33/38; A61K 47/02; A61K 8/046; A61K 8/365; A61K 8/42; A61K 8/64; A61K 2800/22; A61K 2800/244; A61K 47/36; A61K 8/02; A61K 8/0241; A61K 8/732; A61K 8/8129; A61K 8/85; A61K 8/92; A61K 2800/48; A61K 31/015; A61K 31/16; A61K 31/22; A61K 33/00; A61K 45/06; A61K 47/32; A61K 8/06; A61K 8/062; A61K 8/11; A61K 8/19;
(Continued)

(56) References Cited

U.S. PATENT DOCUMENTS

| 5,780,047 A | 7/1998 | Kamiya et al. |
| 2010/0239621 A1* | 9/2010 | Tsujihata ............... A61Q 19/00 424/401 |

(Continued)

FOREIGN PATENT DOCUMENTS

| CA | 2 939 895 A1 | 8/2015 |
| CN | 104717960 A | 6/2015 |

(Continued)

OTHER PUBLICATIONS

WO2015002091A1 translation (Year: 2015).*
(Continued)

*Primary Examiner* — Audrea B Coniglio
(74) *Attorney, Agent, or Firm* — Cheng Law Group, PLLC

(57) ABSTRACT

A cosmetic gel sheet suitable for a cosmetic field or a medical field is provided.

The cosmetic alcogel sheet of the present invention comprises: a water-soluble nonwoven fabric or a water-soluble film; and an alcogel which is laminated on it and contains carboxy group-containing water-soluble polymer, polyalcohol and acid as essential components, and the sheet is characterized in that the water content of the gel is 30% by mass or less. It is more preferred that the carboxy group-containing water-soluble polymer is carboxy group-containing polysaccharides, and the polyalcohol is glycerin. The cosmetic alcogel sheet of the present invention can be manufactured by: drying an aqueous solution containing carboxy group-containing water-soluble polymer, polyalcohol and acid as essential components on a releasable sheet to manufacture gel, and then laminating the gel on a water-soluble nonwoven fabric or a water-soluble film.

16 Claims, No Drawings

(51) Int. Cl.
*A61Q 19/00* (2006.01)
*A61K 8/20* (2006.01)
*A61K 8/73* (2006.01)
*A61K 8/81* (2006.01)
*A61K 8/02* (2006.01)
*A61K 8/34* (2006.01)

(52) U.S. Cl.
CPC .............. *A61K 8/365* (2013.01); *A61K 8/73* (2013.01); *A61K 8/731* (2013.01); *A61K 8/733* (2013.01); *A61K 8/735* (2013.01); *A61K 8/8147* (2013.01); *A61Q 19/00* (2013.01); *A61K 2800/242* (2013.01); *A61K 2800/805* (2013.01)

(58) Field of Classification Search
CPC . A61K 8/25; A61K 8/35; A61K 8/362; A61K 8/442; A61K 8/733; A61K 8/8123; A61K 8/8176; A61K 8/894; A61K 9/703; A61K 2800/31; A61K 2800/5424; A61K 2800/594; A61K 2800/624; A61K 2800/63; A61K 2800/75; A61K 31/08; A61K 31/195; A61K 31/661; A61K 31/728; A61K 47/6957; A61K 8/0204; A61K 8/0229; A61K 8/068; A61K 8/20; A61K 8/26; A61K 8/37; A61K 8/494; A61K 8/4946; A61K 8/553; A61K 8/60; A61K 8/676; A61K 8/737; A61K 8/8111; A61K 8/8152; A61K 8/158; A61K 8/8164; A61K 8/84; A61K 8/922; A61K 9/70; A61K 9/7015; A61K 9/7076; A61K 2800/262; A61K 2800/412; A61K 2800/43; A61K 2800/544; A61K 2800/5922; A61K 2800/74; A61K 2800/782; A61K 2800/87; A61K 2800/95; A61K 31/736; A61K 38/58; A61K 47/42; A61K 47/44; A61K 8/0233; A61K 8/0258; A61K 8/23; A61K 8/27; A61K 8/31; A61K 8/342; A61K 8/347; A61K 8/36; A61K 8/361; A61K 8/368; A61K 8/39; A61K 8/4953; A61K 8/585; A61K 8/645; A61K 8/81; A61K 8/87; A61K 8/88; A61K 8/891; A61K 8/895; A61K 8/898; A61K 9/00; A61K 9/7023; A61K 9/7072; A61K 9/0021; A61K 2800/91; A61K 9/08; A61K 31/122; A61K 31/203; A61K 31/375; A61K 39/12; A61K 47/26; A61K 47/34; A61K 9/7061; A61K 2039/54; A61K 31/737; A61K 36/23; A61K 36/9068; A61K 39/35; A61K 8/981; A61K 8/987; A61K 2039/53; A61K 2039/541; A61K 2039/555; A61K 2800/805; A61K 31/00; A61K 31/136; A61K 31/196; A61K 31/245; A61K 31/7088; A61K 39/00; A61K 39/235; A61K 39/292; A61K 48/0041; A61K 48/005; A61K 48/0075; A61K 6/69; A61K 8/0245; A61K 9/006; A61K 9/0063; A61K 9/7053; A61K 9/7084; A01N 25/16; A01N 25/30; A01N 31/02; A01N 2300/00; A01N 25/06; A01N 59/16; A01N 25/04; A01N 25/14; A01N 25/22; A01N 43/66; A01N 47/44; A01N 25/28; A01N 31/16; A01N 33/12; A61M 37/0015; A61M 2037/0023; A61M 2037/0046; A61M 2037/0053; A61M 2037/0061; A61M 37/00; A61M 2209/00; A61M 2209/06; A61M 2210/0625; A61M 19/00; A61M 2025/0206; A61M 2207/00; A61M 2209/08; A61M 2210/0631; A61M 25/02; A61M 35/003; A61M 5/3298

See application file for complete search history.

(56) References Cited

U.S. PATENT DOCUMENTS

| | | | |
|---|---|---|---|
| 2013/0122069 A1 | 5/2013 | Tojo et al. | |
| 2014/0005615 A1 | 1/2014 | Kishimoto et al. | |
| 2015/0272850 A1* | 10/2015 | Yoneto | ............... C08L 5/08 514/738 |
| 2016/0081906 A1 | 3/2016 | Yoneto | |
| 2017/0007509 A1 | 1/2017 | Kondou et al. | |

FOREIGN PATENT DOCUMENTS

| | | | | |
|---|---|---|---|---|
| CN | 105125420 A | 12/2015 | | |
| CN | 105662917 A | 6/2016 | | |
| EP | 2 910 238 A1 | 8/2015 | | |
| JP | 63-297320 A | 12/1988 | | |
| JP | 3-81213 A | 4/1991 | | |
| JP | 9-216808 A | 8/1997 | | |
| JP | 9-278648 A | 10/1997 | | |
| JP | 11-228340 A | 8/1999 | | |
| JP | 2002-212027 A | 7/2002 | | |
| JP | 2002212027 | * | 7/2002 | ............... A51K 8/00 |
| JP | 2003-518008 A | 6/2003 | | |
| JP | 2005-145895 A | 6/2005 | | |
| JP | 2005-213176 A | 8/2005 | | |
| JP | 2008-137970 A | 6/2008 | | |
| JP | 2009-91342 A | 4/2009 | | |
| JP | 2009-108005 A | 5/2009 | | |
| JP | 2009-108006 A | 5/2009 | | |
| JP | 2009-108007 A | 5/2009 | | |
| JP | 2009-108008 A | 5/2009 | | |
| JP | 2012-30581 A | 2/2012 | | |
| JP | 2012-214454 A | 11/2012 | | |
| JP | 2014-24828 A | 2/2014 | | |
| JP | WO2015002091 | * | 1/2015 | ............... A61K 8/73 |
| KR | 10-2014-0016282 A | 2/2014 | | |
| WO | WO-01/01950 A1 | 1/2001 | | |
| WO | WO-2009/038030 A1 | 3/2009 | | |
| WO | WO-2015/002091 A1 | 1/2015 | | |
| WO | WO-2015/122433 A1 | 8/2015 | | |

OTHER PUBLICATIONS

JP2002212027 abstract translation (Year: 2002).*
International Search Report for the Application No. POT/JP2017/016879 dated Jul. 4, 2017.
Written Opinion of the International Searching Authority (PCT/ISA/237) for the Application No. PCT/JP2017/016879 dated Jul. 4, 2017.
Written Opinion of the International Searching Authority (PCT/ISA/237) for the Application No. PCT/JP2017/016879 dated Jul. 4, 2017 (English Translation mailed Nov. 8, 2018).
Supplementary European Search Report for the Application No. EP 17 789 705.5 dated Oct. 30, 2019.
European Office Action for Application No. EP 17 789 705.5 dated Nov. 17, 2020.
The First Office Action for the Application No. 201780025482.8 from The State Intellectual Property Office of the People's Republic of China dated Dec. 22, 2020.
Korean Office Action for the Application No. 10-2018-7030719 dated Oct. 28, 2021.
"Modern Cosmetic Science and Technology", edited by Qiu Bingyi and Gao Zhihong-Beijing, 1$^{st}$ Edition, China Light Industry Press, Mar. 2016, pp. 1503-1504.
"New Cosmetics", Editor-in-chief: Mitsui Takeo, Translator: Zhang Baoxu-Beijing, 1$^{st}$ Edition, China Light Industry Press, Apr. 1996, p. 138.

(56) References Cited

OTHER PUBLICATIONS

The Second Office Action for the Application No. 201780025482.8 from The State Intellectual Property Office of the People's Republic of China dated Oct. 25, 2021.
Notification of Reasons for Refusal for the Application No. 2021-036539 from Japan Patent Office dated Mar. 2, 2022.

* cited by examiner

ALCOGEL SHEET FOR COSMETIC USE, AND METHOD FOR PRODUCING SAME

TECHNICAL FIELD

The present invention relates to new cosmetics using water-soluble polymer alcogel and a manufacturing method thereof.

BACKGROUND ART

A cosmetic gel sheet is a skin care material, which can give a moist effect, a cool feeling, and a warm feeling when attached to skin. The gel sheet can exhibit the effects on the skin for a long period of time without flowing like skin lotion and milky lotion.

A conventional cosmetic gel sheet, gelled by dissolving hydrophilic resin into water, has been used by making water, a moisturizer, and an electrolyte hold in the sheet. The conventional gel sheet is hydrogel, which contains a large amount of water, and it is essential to crosslink the hydrophilic resin by a crosslinking agent.

A sheet-like pack agent containing collagen and polysaccharide such as chitin, chitosan, alginic acid, and cellulose as components (Patent Document 1), and a skin care cosmetic gel sheet containing polyacrylic acid, polyalcohol, water, and an external crosslinking agent as essential components (Patent Document 2) are known.

A polysaccharide gel sheet containing red seaweed polysaccharide (such as agar and agarose) and fermentation polysaccharide (such as glucomannan and galactomannan) has been reported (Patent Document 3). Furthermore, a gel sheet consisting of hydrophilic polymer with ionic group and water has been reported (Patent Document 4). As the hydrophilic polymer with ionic group, polyvinyl alcohol derivative, (meth)acrylic ester copolymer, cellulose derivative, and polysaccharide derivative (such as xanthan gum and guar gum) are exemplified.

Two component-based sheet-like pack cosmetics prepared by impregnating a water-insoluble gel sheet of amylose with beauty liquid have been reported (Patent Document 5).

A biomedical adhesive gel sheet using natural polymer with hydrophilic group, such as neutral polysaccharides, anionic polysaccharides, cationic polysaccharide and protein (Patent Document 6), or alternatively, a gel sheet containing collagen and a gelling agent and a polyalcohol compound (Patent Documents 7 to 9) has been also reported.

It has been indicated that polysaccharide is suitably mixed in a gel sheet (Patent Documents 10 and 11). As the preferable polysaccharide, neutral polysaccharide (e.g. cellulose, agarose, methyl cellulose, hydroxypropyl cellulose, curdlan, xyloglucan, etc.), anionic polysaccharide (pectic acid, alginic acid, agarose, carboxymethyl starch, carboxymethyl dextran, etc.), and cationic polysaccharide (chitin, chitosan, cationized cellulose, cationized starch, cationized dextran, etc.) are exemplified.

However, these conventional gel sheets which have been published are hydrogel characterized by containing a large amount of water. Therefore, these sheet have a problem that, due to heavy weight of the sheet, the sheet slips down unless a user lies calmly with his or her face upward while the sheet is attached to his or her skin. The conventional gel sheet is of a so-called permanent crosslink type so that extremely high pH or high temperature is needed for breaking the crosslink.

On the other hand, sheet-like cosmetics have also been reported in which hyaluronic acid and a large amount of glycerin are mixed and hyaluronic acid is pseudo-crosslinked by the association of the carboxy groups of hyaluronic acid (Patent Document 12). However, these sheet-like cosmetics were somewhat poor in mechanical strength so that they required careful handling.

PRIOR ART DOCUMENTS

Patent Documents

[Patent Document 1] JP 03-081213 A
[Patent Document 2] JP 11-228340 A
[Patent Document 3] JP 2003-518008 W
[Patent Document 4] JP 2005-145895 A
[Patent Document 5] JP 2005-213176 A
[Patent Document 6] JP 2008-137970 A
[Patent Document 7] JP 2009-091342 A
[Patent Document 8] JP 2009-108005 A
[Patent Document 9] JP 2009-108006 A
[Patent Document 10] JP 2009-108007 A
[Patent Document 11] JP 2009-108008 A
[Patent Document 12] JP 2014-024828 A

SUMMARY OF INVENTION

Technical Problem

The problem to be solved by the present invention is to provide a new and easy-to-use cosmetic gel sheet in which an alcogel is used and which solves the problems of the conventional permanent crosslink-type gel and the new pseudo-crosslink-type hydrogel sheet.

Solution to Problem

The cosmetic gel sheet according to the present invention made for solving the above-mentioned problems is characterized in that the sheet comprises: a water-soluble nonwoven fabric or a water-soluble film; and an alcogel which is held on the water-soluble nonwoven fabric or the water-soluble film and contains carboxy group-containing water-soluble polymer, polyalcohol and acid as essential components.

As used herein, the carboxy group-containing water-soluble polymer refers to water-soluble polymer having carboxy group as a substituent in the molecule.

When a solution containing the carboxy group-containing water-soluble polymer, the acid and the polyalcohol is prepared and its pH is lowered by evaporating the water, the water-soluble polymer is pseudo-crosslinked by the association of the carboxy groups so that the solution is easily gelled. The cosmetic gel sheet of the present invention is an alcogel utilizing this property of the carboxy group-containing water-soluble polymer.

The low water content in the gel sheet, which does not have any physical problem, causes an increased energy cost for the evaporation of the water. Therefore, the water may be practically remained to an extent that a property of the cosmetic alcogel sheet is not damaged.

The water content of the alcogel of the present invention is preferably 30% by mass or less, or more preferably 20% by mass or less. As used herein, the "water content" refers to a water content of the alcogel, and mass of the water-soluble nonwoven fabric or the water-soluble film is not included in the overall mass.

For the alcogel of the present invention, if the water content of the gel exceeds 30% by mass, the water-soluble polymer is insufficiently gelled so that the mechanical strength of the gel sheet is lowered. Therefore, a cosmetic sheet composed only of the gel sheet is problematic in practical use. However, since the present invention utilizes the water-soluble nonwoven fabric or the water-soluble film (hereinafter referred to as the water-soluble nonwoven fabric or the like), the gel sheet is held on the water-soluble nonwoven fabric or the like even if the mechanical strength of the gel sheet itself is lowered. Thus the gel sheet may have a more water content. However, if the gel sheet includes too much amount of water, the water may be transferred into the water-soluble nonwoven fabric or the like as a liner, and the water-soluble nonwoven fabric or the like may be dissolved.

Although carboxy group-containing synthetic polymers, such as polyacrylic acid and copolymer thereof, and carboxy group-containing polysaccharides can be considered as the carboxy group-containing water-soluble polymer, the latter is more preferable in the present invention. This is because the carboxy group-containing water-soluble polymer, which is synthetic polymer, has a malodor due to residual monomer.

The cosmetic alcogel sheet is not required to contain water-soluble divalent ions as in the case of the hydrogel sheet. In the case of the conventional hydrogel sheet containing a large amount of water (in a proportion of 70% by mass or more based on the gel sheet), for gelling the carboxy group-containing water-soluble polymer, crosslink by water-soluble divalent metal ions is required (Patent Documents 1 and 2). According to the present invention, since the mutual association of the carboxy group by reducing the water content in the gel is utilized, the metal salt is not required.

Furthermore, in the gel sheet with a large amount of water and the mutual association by the divalent metal ions, even if skin is massaged with water after the gel sheet is applied, the carboxy group-containing polysaccharide cannot be dissolved into the water. A mechanism of the gel association is distinctively different between the conventional hydrogel sheet and the cosmetic gel sheet according to the present invention, and as a result, they have different effects.

Although the carboxy group-containing water-soluble polymer is gelled in an acidic solution by the mutual association of the carboxy group, if pH approaches neutral, gel structure is broken and becomes an aqueous solution. Namely, the gel structure is reversibly in the gel state or in the soluble state according to pH change. Therefore, when the sheet is attached to skin in the gel state and then the skin is massaged with an appropriate amount of water, polysaccharide gel is solubilized, so the polysaccharide and a blended valuable component can be effectively absorbed into the skin.

In an acid concentration at which pH of the aqueous solution is 2.0 or less, since the gel structure is strong, the structure hardly becomes the soluble state even if the appropriate amount of water is added to massage. As used herein, the appropriate amount refers to an amount so as not to flow down from a face when the cosmetic gel sheet is attached to the face and then water is added. It is practically meaningless that water is added in too much amount so as not to be remained on a face.

The polyalcohol has a property for generating heat when brought into contact with water. The polyalcohol as a maximum component in the alcogel sheet generates heat when the gel sheet is attached to skin and then water is added, so a comfortable warm feeling is given to the skin. The conventional gel sheet does not significantly generate heat due to its large water content, whereas the alcogel sheet according the present invention with low water content can give the warm feeling.

As the carboxy group-containing polysaccharide, xanthan gum, gellan gum, alginic acid, carboxymethyl cellulose, hyaluronic acid with carboxy group, and the like are preferably used. They may be partially converted to a salt such as sodium salt or potassium salt.

Molecular weight of the carboxy group-containing water-soluble polymer is preferably within a range from approximately $5*10^4$ to $5*10^6$ Dalton. Different water-soluble polymer, or the same water-soluble polymer with different molecular weight may be mixed for use so long as the molecular weight is within this range. Also, water-soluble polymer within this molecular weight range and water-soluble polymer with lower molecular weight than this range can be mixed for use.

As the acid used in the present invention, monobasic acid such as hydrochloric acid, acetic acid, and lactic acid, polybasic acid such as citric acid, oxalic acid, and tartaric acid, and the like can be used. Citric acid, tartaric acid, and lactic acid are particularly preferable. Furthermore, two or more kinds of the acid can be mixed for use.

The polyalcohol used in the present invention is not particularly limited, but glycerin, propylene glycol, ethylene glycol, polyethylene glycol, 1,3-butylene glycol, dipropylene glycol, sorbitol, and the like can be used. Among them, glycerin is particularly preferable.

The content of each component in the cosmetic alcogel sheet of the present invention is as follows. The content of the carboxy group-containing water-soluble polymer is preferably within a range from 0.1% by mass to 10% by mass based on the whole gel. If the content of the carboxy group-containing water-soluble polymer is less than 0.1% by mass, the gel is softened so that the gel with an excellent elasticity cannot be formed. Whereas, if the content is more than 10% by mass, the gel is hardened so that the gel with the excellent elasticity cannot be formed and adhesiveness to skin becomes poor.

The content of the polyalcohol is preferably within a range from 10 to 1,000 or more parts by mass, more preferably within a range from 30 to 500 parts by mass, based on 1 part by mass of the carboxy group-containing water-soluble polymer. If the content of the polyalcohol is less than 10 parts by mass, the sheet becomes hard gel rather than the gel with the excellent elasticity having appropriate skin attachability. Whereas, if the content is more than 1,000 parts by mass, the gel is softened or the gel formation becomes impossible.

The content of the acid is adjusted so that the pH of the raw material aqueous solution is appropriate for the association of the carboxy group-containing water-soluble polymer. For example, when 120 parts by mass of water are used based on 1 part by mass of the carboxy group-containing water-soluble polymer, the content of the acid is preferably adjusted to a value required for setting pH of the aqueous solution to 4.5 to 2.0. If the content of the water is lower than the above-described amount, pH may be set to a lower value, whereas, if the content of the water is larger, pH may be set to a larger value. In the case of the exemplified water content, if pH is 4.5 or more, gel with sufficient strength cannot be obtained when the water is dried. Whereas, pH of 2.0 or less is not preferable since the raw material aqueous solution is likely to be easily gelled before the water is dried, and further, even if the gel sheet can be generated by drying the water, the gel sheet gives stimulus to a face when attached.

For the carboxy group-containing polysaccharide alcogel, the water, which is originally a maximum component of the aqueous solution, is volatilized in a drying process, so that the polyalcohol becomes the maximum component in the alcogel.

Although the alcogel sheet of the present invention is gelled due to the pseudo-crosslinking between the carboxy group-containing polymers so that it has some mechanical strength, the strength is at most 0.1 N/cm$^2$ as a rupture stress measured by means of a tension testing machine, and therefore the sheet is likely to be broken with careless handling.

However, the alcogel sheet itself of the present invention has improved safeness and handling property because it is held on the water-soluble nonwoven fabric or the like. With the water-soluble nonwoven fabric or the like as a liner, the alcogel sheet of the present invention still maintains the following characteristics as fundamental properties: (1) it causes warm feeling when applied on the skin; and (2) after application on the face skin, it is solubilized by massage with an appropriate amount of water. Furthermore, the handling property and usability for users are excellently improved, which enhances its significance as cosmetics.

As the water-soluble nonwoven fabric, those composed of water-soluble polymer fibers can be suitably utilized. It was confirmed that G-Polymer, the water-soluble PVOH manufactured by The Nippon Synthetic Chemical Industry Co., Ltd. and Kuralon K-II, the PVOH nonwoven fabric manufactured by KURARAY CO., LTD were suitable among the commercial products. For practically lining the gel sheet with the water-soluble nonwoven fabric, the adhesiveness of the gel sheet may be utilized to directly laminate the water-soluble nonwoven fabric. However, the laminate strength can be increased by thinly applying a water-soluble adhesive onto the water-soluble nonwoven fabric and then laminating it onto the gel sheet.

As the water-soluble film, those composed of the same polyvinyl alcohol as the nonwoven fabric can be suitably utilized. It is desired that a degree of saponification is not high for improved water-solubility. Specifically, Solublon TS or Solublon CA manufactured by AICELLO CORPORATION and the like can be used.

In the cosmetic alcogel sheet, the valuable component such as cosmetic and pharmaceutical components can be blended within a range which does not affect the object and an effect of the present invention. Particularly, it is advantageous for application as cosmetics and a quasi-drug. The blendable component includes, for example, whitening component, anti-wrinkle component, anti-inflammatory component, blood circulation promoting component, anti-microbial component, anti-pruritic component, various vitamins and derivatives thereof, anti-oxidative component, pigment, oil component, fragrance, and the like. The cosmetic and pharmaceutical components to be blended can be added to the raw material aqueous solution.

The whitening component is not particularly limited, but, for example, vitamin C derivative such as ascorbic acid phosphoric ester magnesium salt, ascorbic acid glucoside and salts and acyl derivative thereof, ethylascorbic acid, and ascorbyl palmitate, α-arbutin, β-arbutin, kojic acid, placenta extract, cysteine, glutathione, ellagic acid, rucinol, tranexamic acid, baicalein, adenosine and phosphoric acid sodium salt thereof, astaxanthin, deer horn shaped *Ganoderma lucidum*, oil-soluble licorice, lavender, lempuyang, burnet, resveratrol, *Ganoderma lucidum*, extracts and tincture thereof, or components contained therein, and the like are included.

The anti-wrinkle component is not particularly limited, but, for example, retinoid such as retinol, retinoic acid, retinol acetate, and retinol palmitate, α-hydroxy acid such as citric acid, fruit acid, glycolic acid, and lactic acid, α-hydroxyl acid cholesterol, rutin derivative, N-methylserine, elastin, collagen, sericin, *Centella asiatica* extract, *Scutellaria baicalensis* extract, and the like are included.

The anti-inflammatory component is not particularly limited, but, for example, glycyrrhetinic acid, ghycyrrhetinic acid 2K, allantoin, epsilon-aminocaproic acid, azulene, shikonin, tranexamic acid, and *Coptis japonica*, licorice, Terminalia, yarrow, lithospermum root, comfrey, aloe, butcher's bloom, horse chestnut, peach leaf, loquat leaf, and extracts and tincture thereof, or components contained therein, and the like are included.

The blood circulation promoting component is not particularly limited, but, for example, vitamin E, nicotinic acid, nicotinic acid amide, benzyl nicotinate, nicomol, caffeine, capsaicin, nonanoic acid vanillylamide, shogaol, gingerol, and the like are included.

The anti-microbial component is not particularly limited, but, for example, cationic surfactant such as isopropyl methylphenol, triclosan, triclocarban, trichloro-hydroxyphenol, halocarbon, benzalkonium chloride, and benzethonium chloride, photosensitizer, zinc oxide, titanium oxide, chitin, chitosan, hinokiol, anise, and the like are included.

The anti-pruritic component is not particularly limited, but, for example, diphenhydramine hydrochloride, chlorpheniramine maleate, crotamiton, glycyrrhizin acid, menthol, camphor, rosemary oil, capsaicin, nonanoic acid vanillylamide, dibucaine, and the like are included.

The vitamins are not particularly limited, but, for example, as oil-soluble vitamins, vitamin A oil, cod-liver oil, retinol acetate, retinol palmitate, retinol, dehydroretinol, vitamin $A_3$, retinoic acid, vitamin D, vitamin $D_2$ (ergocalciferol), vitamin $D_3$ (cholecalciferol), vitamin derivative, vitamin E (tocopherol), dl-α-tocopherol acetate, dl-α-tocopherol, tocopherol butyrate, tocopheryl nicotinate, nicotinic acid benzyl ester, natural vitamin E, vitamin K, vitamin U, and the like are included. Also, as water-soluble vitamins, vitamin $B_1$ (thiamin), vitamin $B_2$ (riboflavin tetrabutyrate), vitamin $B_6$ (fatty acid ester such as pyridoxine dicaprylate and pyridoxine dipalmitate), vitamin $B_{12}$ (cobalamin), vitamin $B_{13}$, vitamin $B_{14}$, vitamin $B_{15}$ (pangamic acid), folic acid, carnitine, thioctic acid, pantothenyl alcohol, pantothenyl ethyl ether, pantothenic acid, nicotinic acid, nicotinic-acid amide, choline, inositol, vitamin C (ascorbic acid), ascorbyl stearate, ascorbyl pantothenate, ascorbyl dipalmitate, vitamin H (biotin), vitamin P (hesperidin), Apprecier, and the like are included.

The anti-oxidative component is not particularly limited, but, for example, polyphenols such as anthocyanin, catechin, green tea polyphenol, and apple polyphenol, carotenoid such as ascorbic acid, sodium ascorbate, sodium sulfate ascorbate, β-carotene, and astaxanthin, β-diketone such as tocopherols, tocopherol acetate, natural vitamin E, tocomonoenol, tocotrienol, and curcumin, lignin such as sesamin and sesamolin, phenol such as eugenol, and the like are included.

Anti-allergic component is not particularly limited, but, for example, glycyrrhetinic acid derivative such as glycyrrhetinic acid and glycyrrhetinic acid 2K, licorice, *chlorella*, comfrey, moutan cortex, *Tilia cordata, Isodon japonicus*, sage, shiso, mugwort, extracts and tincture thereof or components contained therein, and the like are included.

The oil component includes olive oil, squalane, squalene, paraffin oil and the like. Adding the oil component improves the feeling of the alcogel sheet with respect to the skin. Since the oil component is likely to cause phase separation when added in a large amount, the amount of the oil component in the alcogel sheet of the present invention is preferably 5% by mass or less.

The cosmetic alcogel sheet according to the present invention can be manufactured by: uniformly dissolving the carboxy group-containing water-soluble polymer, the acid, and the polyalcohol into water; suitably drying and transpiring the water to make the gel sheet of an intended form; and then laminating the gel sheet onto the water-soluble nonwoven fabric or the like.

Specifically, an aqueous solution containing the carboxy group-containing water-soluble polymer, the polyalcohol, and the acid is mixed for preparation with a propeller type rotary stirrer. The prepared aqueous solution is applied on a polyethylene terephthalate film in a uniform thickness, then it is dried with hot air, and thereby a transparent gel sheet with the uniform thickness is manufactured. In the drying process of the aqueous solution, the drying is carried out so that the water content of the gel becomes 40% by mass or less. Preferably, the water content of the gel is 30% by mass or less. This is because there is a possibility that, drying of the gel would proceed in the following step of integrating the water-soluble nonwoven fabric or the like with the gel sheet.

Thereafter, the water-soluble nonwoven fabric or the like is laminated and pressed to integrate the nonwoven fabric and the gel sheet. The gel sheet contains water though it is only 30% by mass or less, and the nonwoven fabric or the film is water-soluble. Therefore the water and the valuable components in the gel sheet is transferred into the nonwoven fabric or the like so that the gel sheet and the nonwoven fabric or the like forms an integrated sheet. Then the gel sheet is cut into circle, oval, comma shape, or face shape to obtain a product as sheet-like cosmetics. The nonwoven fabric or the like may contain polyalcohol such as glycerin for facilitating the water-solubility.

The weight per unit area of the nonwoven fabric of the present invention is suitably 5 to 100 $g/m^2$, and the thickness of the film is preferably 5 to 50 μm.

For the cosmetic gel sheet of the present invention, the thickness of the gel sheet alone is 40 to 600 μm, preferably 80 to 250 μm, and the thickness of the whole cosmetic gel sheet of the present invention is 50 to 700 μm, preferably 100 to 350 μm.

When the cosmetic alcogel sheet of the present invention is applied on a face, it generates heat due to reaction between water vapor in the air passing through the nonwoven fabric and polyalcohol or due to absorption of water on the surface of the face, so that it gives warm feeling to the face.

When the cosmetic alcogel sheet of the present invention is applied on a face and then the face is massaged with adding an appropriate amount of water, the alcogel sheet is gradually dissolved with giving warm feeling to the face. This is because the gel is dissolved by increasing water content and thus a pH value. The water-soluble nonwoven fabric or the like is dissolved simultaneously with the gel by supplying water.

Advantageous Effects of Invention

In the cosmetic alcogel sheet according to the present invention, water is not an essential component and the carboxy group-containing water-soluble polymer is gelled in the polyalcohol. This type of the cosmetic alcogel sheet has the following characteristics.

(1) Since the low water content is not suitable for propagation of microorganism, an antiseptic agent is not required.

(2) A main component is the polyalcohol, so the alcohol generates heat by hydration to give a comfortable feeling to skin when the skin is massaged with water (hot water) after application of the alcogel sheet.

(3) Stability of a cosmetic valuable component unstable to water is increased.

The cosmetic alcogel sheet according to the present invention utilizes an excellent original property of the water-soluble polymer and the polysaccharide. The carboxy group-containing water-soluble polymer gel which is not chemically crosslinked gives a warm feeling by the hydration of the polyalcohol when a small amount of water is added after application to skin, and, when the skin is massaged, the gel is dissolved, so the blended component is penetrated into the skin. Then, even when the gel is washed away with water, the effects are sustained to give the warm feeling, a moisture feeling, and a smooth feeling to the skin. Therefore, the gel is useful as a material to be used in a cosmetic field. These effects have not been observed in the conventional hydrogel sheet.

The cosmetic alcogel sheet of the present invention has improved mechanical strength by laminating it onto the water-soluble nonwoven fabric or the like, so that it is easier to handle than conventional products.

DESCRIPTION OF EMBODIMENTS

Hereinafter, the present invention will be described with reference to Examples, but the present invention is not of course limited to the following Examples.

Manufacturing Method of Examples 1 to 6 as Well as Comparative Examples 1 and 2

Aqueous solutions containing carboxy group-containing water-soluble polymer, polyalcohol and acid were stirred and mixed according to blending ratios (part by mass) described in Table 1 with a propeller type rotary stirrer to prepare raw material aqueous solutions. Tocopherol and Apprecier were dissolved into a small amount of ethanol and then added. The prepared raw material aqueous solutions were applied on polyethylene terephthalate films with a uniform thickness of 25 μm and then dried at 80° C. for 5 to 30 minutes with a gear type oven to obtain a cosmetic gel sheet with a thickness of approximately 200 μm. A water-soluble adhesive solution with a thickness after drying of about 10 μm was applied onto the water-soluble nonwoven fabric and dried at 80° C. for 20 minutes. Then the gel sheet was put onto the water-soluble nonwoven fabric and pressed by a roller to laminate the gel sheet and the nonwoven fabric.

The water-soluble nonwoven fabric was used for Examples 1 to 5, and the water-soluble film was used for Example 6. The resulting sheets were cut to subject them to various evaluation.

TABLE 1

| Components | Carboxy group-containing water-soluble polymer | | | | | | |
|---|---|---|---|---|---|---|---|
| | Xanthan gum | Gellan gum | Alginic acid | Hyaluronic acid | Polyacrylic acid | Glycerin | Ethylene Glycol |
| Example | | | | | | | |
| 1 | 1 | | | | | 80 | |
| 2 | | 1 | | | | 60 | |
| 3 | | | 1 | | | 50 | |
| 4 | | | | 1 | | 60 | |
| 5 | | | | | 1 | | 50 |
| 6 | | | | 1 | | 60 | |
| Comparative Example | | | | | | | |
| 1 | 1 | | | | | 80 | |
| 2 | | 1 | | | | 60 | |

| Components | Acid | | | Valuable component | | Water | pH of raw material aqueous solution |
|---|---|---|---|---|---|---|---|
| | Citric Acid | Lactic Acid | Hydrochloric acid | Tocopherol | Apprecier | | |
| Example | | | | | | | |
| 1 | | | 0.5 | | | 120 | 3.4 |
| 2 | | 0.9 | | 0.05 | | 120 | 3.5 |
| 3 | 0.6 | | | | | 120 | 3.6 |
| 4 | 0.6 | | | | | 90 | 3.5 |
| 5 | 0.5 | | | | 0.05 | 100 | 3.2 |
| 6 | 0.5 | | | 0.05 | | 100 | 3.2 |
| Comparative Example | | | | | | | |
| 1 | | | 0.5 | | | 120 | 3.4 |
| 2 | | 0.9 | | 0.05 | | 120 | 3.5 |

Standards and sources of each raw material are as follows. Hyaluronic acid with molecular weight of about 800,000 (FCH-80, Kikkoman Biochemifa Company) was used as hyaluronic acid. As the other raw materials, glycerin (concentrated glycerin, MIYOSHI OIL & FAT CO., LTD.), citric acid (NACALAI TESQUE, INC.), trisodium ascorbyl palmitate phosphate (Apprecier, SHOWA DENKO K.K.), tocopherol (NACALAI TESQUE, INC.), xanthan gum (SANSHO Co., Ltd.), gellan gum (Wako Pure Chemical Industries, Ltd.), CMC1260 as carboxymethyl cellulose (DAICEL FINECHEM LTD.), and alginic acid (Kikkoman Biochemifa Company) were used. Lactic acid, ethylene glycol, hydrochloric acid, and acetic acid of guaranteed reagent (NACALAI TESQUE, INC.) were used. G-Polymer, the water-soluble PVOH with the weight per unit area of 30 g/m$^2$ (The Nippon Synthetic Chemical Industry Co., Ltd.) was used as the water-soluble nonwoven fabric. Solublon TS (thickness of 30 μm, AICELLO CORPORATION) was used as the water-soluble film. Liquidyn AR-2090 (VIGteQnos Corporation) was used as the water-soluble adhesive.

The amounts of the hydrochloric acid and the acetic acid are shown in converted parts by mass from the aqueous solution reagent.

(Comparison of Properties Among the Manufactured Polysaccharide Gel Sheets)

Evaluation results of the polysaccharide gel sheets in Examples 1 to 6 and Comparative Examples 1 to 2 are summarized in Table 2. Note that, since the gels of Comparative Examples were not in a sheet form but in a liquid form containing a large amount of water, the various tests which postulate the object to be tested should be a gel sheet were meaningless, so that these gels were not evaluated.

1. Results of Properties Observation

Observation results of flexibility and elasticity by naked eyes and touch are shown. "A" means that both flexibility and elasticity were sufficient. "B" means that flexibility was sufficient and elasticity was weak but not problematic in practical use. "C" means that the object to be tested was not a gel but in a liquid form.

2. Results of Water Content Measurement

Measurement results of water content in the gel are shown. The water content measurements were determined from mass reduction values before and after heating samples at 90° C. for 1 hour.

3. Results of Test on Adhesiveness to Skin

Test results on adherence to skin when the polysaccharide gel sheets (2 cm*2 cm) were applied inside a forearm of a human volunteer are shown. "A" means excellent adherence.

4. Results of Test on Warm Feeling

Test results on a warm feeling to skin when the polysaccharide gel sheets (2 cm*2 cm) were applied inside a forearm of a human volunteer are shown. "A" means strong warm feeling to the skin, and "B" means some warm feeling.

5. Test on Solubility

The polysaccharide gel sheets (2 cm*2 cm) were applied on a forearm of a human volunteer, on which 1 ml of water was dripped and then the skin was massaged over the sheets for 3 minutes to observe solubility of the gel. "A" means complete dissolution.

6. Test on Handling Property

"A" means that the gel sheet has good mechanical strength and thus is not broken by careless handling to some degree, so that the gel sheet is extremely easy to handle.

TABLE 2

|  |  | Drying time (min.) | Water content, % by mass | Property | Test on adhesiveness to Skin | Test on warm feeling | Test on solubility | Test on handling property |
|---|---|---|---|---|---|---|---|---|
| Example | 1 | 30 | 9.4 | A | A | A | A | A |
|  | 2 | 30 | 9.2 | A | A | A | A | A |
|  | 3 | 25 | 18.5 | A | A | A | A | A |
|  | 4 | 25 | 17.8 | A | A | A | A | A |
|  | 5 | 20 | 25.6 | B | A | B | A | A |
|  | 6 | 25 | 18.5 | A | A | A | A | A |
| Comperative Example | 1 | 10 | 55.6 | C |  | Impossible |  |  |
|  | 2 | 5 | 77.4 | C |  | Impossible |  |  |

It can be found from Table 1 that the compositions of the aqueous solutions in both Examples and Comparative Examples are suitable for the raw material solution of the alcogel sheet.

It can be found from Table 2 that, for stable generation of the alcogel, the raw material aqueous solution needs to be dried to the water content of 30% by mass or less, preferably 20% by mass or less.

What is claimed is:

1. A cosmetic alcogel sheet comprising:
   a water-soluble nonwoven fabric having a weight per unit area of 5 to 100 g/m$^2$ or a water-soluble film having a thickness of 5 to 50 μm; and
   a gel sheet comprising an alcogel which is held on the water-soluble nonwoven fabric or the water-soluble film and contains carboxy group-containing water-soluble polymer, polyalcohol and acid as essential components,
   wherein the gel sheet alone has a thickness of 40 to 600 μm, and
   wherein a water content of the alcogel is 30% by mass or less.

2. The cosmetic alcogel sheet according to claim 1, wherein
   the water content of the alcogel is 20% by mass or less.

3. The cosmetic alcogel sheet according to claim 1 or 2, characterized in that that the carboxy group-containing water-soluble polymer is carboxy group-containing polysaccharides.

4. The cosmetic alcogel sheet according to claim 1 or 2, characterized in that that a content of the polyalcohol is 10 to 1000 parts by mass based on 1 part by mass of the carboxy group-containing water-soluble polymer.

5. The cosmetic alcogel sheet according to claim 1 or 2, characterized in that that the cosmetic alcogel sheet generates heat when attached on a skin.

6. The cosmetic alcogel sheet according to claim 3, characterized in that that the carboxy group-containing water-soluble polymer is one or more compounds selected from a group consisting of xanthan gum, gellan gum, alginic acid, hyaluronic acid and carboxymethyl cellulose.

7. The cosmetic alcogel sheet according to claim 1 or 2, characterized in that that the polyalcohol is glycerin.

8. The cosmetic alcogel sheet according to claim 1 or 2, characterized in that that the acid is one or more compounds selected from a group consisting of citric acid, tartaric acid, lactic acid and hydrochloric acid.

9. A method of manufacturing a cosmetic alcogel sheet, characterized in that:
   an aqueous solution comprising a carboxy group-containing water-soluble polymer, a polyalcohol and an acid as essential components is applied on a film or poured into a tray;
   the aqueous solution is dried to a water content of 30% by mass or less to form a gel sheet; and
   a water-soluble nonwoven fabric having a weight per unit area of 5 to 100 g/m$^2$ or a water-soluble film having a thickness of 5 to 50 μm is laminated to manufacture the cosmetic alcogel sheet,
   wherein the gel sheet alone has a thickness of 40 to 600 μm.

10. The method of manufacturing a cosmetic alcogel sheet according to claim 9, characterized in that, when manufacturing the alcogel sheet, a content of the acid in the aqueous solution is an appropriate amount for allowing a pH of the aqueous solution to be 2.0 to 4.5.

11. The cosmetic alcogel sheet according to claim 1, wherein
   the gel sheet alone has a thickness of 80 to 250 μm.

12. The cosmetic alcogel sheet according to claim 1, wherein
   the gel sheet alone has a thickness of 80 to 250 μm, and the cosmetic alcogel sheet has a thickness of 100 to 350 μm.

13. The method of manufacturing a cosmetic alcogel sheet according to claim 9, wherein
   the gel sheet alone has a thickness of 80 to 250 μm.

14. The method of manufacturing a cosmetic alcogel sheet according to claim 9, wherein
   the gel sheet alone has a thickness of 80 to 250 μm, and the cosmetic alcogel sheet has a thickness of 100 to 350 μm.

15. The cosmetic alcogel sheet according to claim 1, further comprising paraffin oil.

16. The cosmetic alcogel sheet according to claim 1, further comprising a polyphenol.

* * * * *